(12) United States Patent
Lin et al.

(10) Patent No.: US 10,519,319 B2
(45) Date of Patent: Dec. 31, 2019

(54) THREE-DIMENSIONAL PRINTING METHODS AND MATERIALS FOR MAKING DENTAL PRODUCTS

(71) Applicant: NATIONAL YANG-MING UNIVERSITY, Taipei (TW)

(72) Inventors: Yuan-Min Lin, Taipei (TW); Hsuan Chen, Taipei (TW); Shyh-Yuan Lee, Taipei (TW); Pin-Ju Huang, Taipei (TW)

(73) Assignee: NATIONAL YANG-MING UNIVERSITY, Taipei (TW)

( * ) Notice: Subject to any disclaimer, the term of this patent is extended or adjusted under 35 U.S.C. 154(b) by 17 days.

(21) Appl. No.: 15/914,784

(22) Filed: Mar. 7, 2018

(65) Prior Publication Data
US 2018/0258290 A1    Sep. 13, 2018

Related U.S. Application Data

(60) Provisional application No. 62/468,107, filed on Mar. 7, 2017.

(51) Int. Cl.
| | |
|---|---|
| *C08F 2/46* | (2006.01) |
| *C08F 2/50* | (2006.01) |
| *C08G 61/04* | (2006.01) |
| *C09D 4/00* | (2006.01) |
| *G03G 9/087* | (2006.01) |
| *G03F 7/075* | (2006.01) |
| *G03F 7/004* | (2006.01) |
| *A61C 13/00* | (2006.01) |
| *G03F 7/038* | (2006.01) |
| *G03F 7/039* | (2006.01) |
| *G03G 9/083* | (2006.01) |
| *G03F 7/029* | (2006.01) |

(52) U.S. Cl.
CPC ............ *C09D 4/00* (2013.01); *A61C 13/0019* (2013.01); *G03F 7/0043* (2013.01); *G03F 7/029* (2013.01); *G03F 7/038* (2013.01); *G03F 7/039* (2013.01); *G03F 7/0755* (2013.01); *G03G 9/0833* (2013.01); *G03G 9/08728* (2013.01)

(58) Field of Classification Search
CPC .... C09D 4/00; A61C 13/0019; G03G 9/0728; G03G 9/0833; G03F 7/0755; G03F 7/039; G03F 7/029; G03F 7/0043; G03F 7/038; G03F 7/0047; G03F 7/027; G03F 7/0037
USPC ................. 522/64, 6, 71, 1, 189, 184; 520/1
See application file for complete search history.

(56) References Cited

U.S. PATENT DOCUMENTS

| | | | |
|---|---|---|---|
| 2005/0154081 A1* | 7/2005 | Yin | A61K 6/083 523/115 |
| 2014/0162216 A1* | 6/2014 | Craig | A61C 13/0022 433/201.1 |
| 2015/0257985 A1* | 9/2015 | Sadowsky | A61K 6/083 523/115 |
| 2018/0078348 A1* | 3/2018 | Ruppert | A61C 13/0004 |

\* cited by examiner

*Primary Examiner* — Jessica Whiteley
(74) *Attorney, Agent, or Firm* — Muncy, Geissler, Olds & Lowe, P.C.

(57) ABSTRACT

The present invention provides a three-dimensional printing article for making dental products and the preparation method thereof, which comprises: Ethoxylated bisphenol A dimethacrylate, Diurethane dimethacrylate, Triethylene glycol dimethacrylate, and Diphenyl (2,4,6-trimethylbenzoyl) phosphine oxide. It not only improves the present time-consuming and labor-intensive dental device making, but also can be used in mass production of dental devices.

10 Claims, 3 Drawing Sheets

201 — Pouring the three-dimensional printing article for making dental productsinto a container 202 — Obtaining a plurality of continuously sectional drawings of a dental prosthesis simple, wherein there is a sectional distance of the dental prosthesissimple between each 203 — Choosing the top ofthe drawings, forming a sheet model as the chosen drawingthroughfocusing an intensive irradiation light sourceon the bottom of the container 204 — Moving the sheet model upward for the sectionaldistance, and repeating step 203 throughchoosingthe next ofthe drawings until the bottom of the drawings, each of the sheet models is sequentiallystacked to form thedental prosthesis

Fig 2

THREE-DIMENSIONAL PRINTING METHODS AND MATERIALS FOR MAKING DENTAL PRODUCTS

CROSS-REFERENCE TO RELATED APPLICATIONS

This Non-provisional application claims priority under 35 U.S.C. § 119(a) on Patent Application No. 62/468,107 filed in American United States Mar. 7, 2017, the entire contents of which are hereby incorporated by reference.

FIELD OF THE INVENTION

The present invention relates generally to a three-dimensional printing article for making dental products, and more particularly to a mixture of the components of Ethoxylated bisphenol A dimethacrylate, Diurethane dimethacrylate, Triethylene glycol dimethacrylate and a photo-initiator

BACKGROUND OF THE INVENTION

Typical three-dimensional printing technologies include: (1) stereolithography appearance (SLA), which uses photopolymers and irradiation of ultraviolet laser for solidification; (2) selective laser sintering (SLS), which uses granule powder of thermoplastic materials (including polymers like nylon, metals like bronze alloy and titanium alloy, as well as ceramics and glass) to be fused by high power laser; (3) fused deposition modeling (FDM), referring to immediate solidification of sprayed molten thermoplastic materials or eutectic metal powder; (4) laminated object manufacturing (LOM), which uses glue to bond paper or plastic films and then uses laser for formation; (5) ink-jet printing, which sprays fine powder of different materials and uses a bonding agent to cover the materials, and then prints the next layer. Ink-jet printing can also print living cells and biological materials simultaneously to build a three-dimensional biological scaffold with different tissues, or even a living organ.

With the development of dental implantation, there are more and more breakthroughs and applications of core technologies. However, at present, dental implantation is still known for its high price and high risk, because it requires hours of meticulous work by dentists with high technological level and rich operational experience, and a series of tasks including diagnosis, narcosis, selection of implants, tooth preparation modeling, design and production of a dental prosthesis, denture modification and mounting. The application of three-dimensional printing technology in the field of dental implantation is to integrate the technologies of oral scan, oral image processing and three-dimensional printing, and to use technological systems of "digital image capture and reconstruction, CAD/CAM professional design, standard three-dimensional printing and manufacturing, and standardized implantation", so that, before implantation, the final outcome can be seen from a computer. Before operation, a CT scan of the patient's oral cavity is conducted, and then accurate data is input into a designated design software program, through which, a three-dimensional design of the implantation position is made. Then, an appropriate type of implant is selected, and operation is conducted on the basis of a navigational template to implant the denture and prosthesis. And finally, an ergonomic modification is carried out according to the patient's need. This method can avoid problems like misjudgment of the dentist due to two-dimensional scan image overlay, and reduce risks caused by insufficient skill and experience of the dentist. It can also reduce the workload of dentists while enhancing treatment safety. By sharing digital resources, diagnosis and treatment become "economy".

The previous processes to make a dental device are time-consuming and labor-intensive, and massive production cannot be fulfilled easily. However, with the current three-dimensional printing and manufacturing technique, the accuracy of a final finished product can be enhanced to the allowance level of only several microns. The three-dimensional printing technology truly provides a big help for the dental industry which requires precision manufacturing. Therefore, a temporary dental prosthesis can be obtained within the time of treatment, and the patient's waiting time is significantly reduced. At present, most three-dimensional printing article used in the domestic dental industry are provided by overseas suppliers, and the cost is very high. Therefore, there is an urgent need to develop a low-cost three-dimensional printing article for making dental products.

SUMMARY OF THE INVENTION

In view of above, the present invention provides a material mainly comprising conventionally used resin for dental products, with an additional dental filling material as the filler for the three-dimensional printing resin material. The present invention has a good biological compatibility, with no toxicity to harm the human body, and can reduce the cost of dental materials.

The aim of the present invention is to provide a three-dimensional printing article for making dental products, which comprises: a compound made of 20 to 80 wt % (percentage by weight) ethoxylated bisphenol A dimethacrylate, 0 to 75 wt % diurethane dimethacrylate and 0 to 10 wt % triethylene glycol dimethacrylate; and 0.01 to 10 wt % photo-initiator.

The present invention further provides a method to prepare said three-dimensional printing article for making dental products, which includes the following steps: (a) mixing Ethoxylated bisphenol A dimethacrylate, Diurethane dimethacrylate, and Triethylene glycol dimethacrylate at room temperature to form a compound, wherein, the proportional rate between Ethoxylated bisphenol A dimethacrylate, Diurethane dimethacrylate, and Triethylene glycol dimethacrylate is 20 to 80 wt %:0 to 75 wt %:0 to 10 wt %; and (b) adding 0.01 to 10 wt % photo-initiator for forming a three-dimensional printing article for making dental products.

The present invention further provides a method to make dental products using said three-dimensional printing article, which includes the following steps: (a) pouring the three-dimensional printing article for making dental products into a container; (b) obtaining a plurality of continuously sectional drawings of a dental prosthesis simple, wherein there is a sectional distance of the dental prosthesis simple between each drawing; (c) choosing the top of the drawings, forming a sheet model as the chosen drawing through focusing an intensive irradiation light source on the bottom of the container; and (d) moving the sheet model upward for the sectional distance, and repeating step (c) through choosing the next of the drawings until the bottom of the drawings, each of the sheet models is sequentially stacked to form the dental prosthesis.

As disclosed above, the three-dimensional printing article for making dental products provided by the present invention features dominant materials of resin with an addition of inorganic filling materials as fillers. The finished product has a good biological compatibility. Also, as the three-dimensional printing article for making dental products is in a wax-like state, it can be injected or carried by a container to be used by current three-dimensional printing machines.

Although the present invention has been described in terms of specific exemplary embodiments and examples, it will be appreciated that the embodiments disclosed herein are for illustrative purposes only and various modifications and alterations might be made by those skilled in the art without departing from the spirit and scope of the invention as set forth in the following claims.

BRIEF DESCRIPTION OF THE DRAWINGS

FIG. 2 is a flow chart of the method to make dental products using the three-dimensional printing article of the present invention.

DETAILED DESCRIPTION OF THE INVENTION

The present invention provides a three-dimensional printing article for making dental products, comprising: a compound made of about 20 to about 80 wt % of Ethoxylated bisphenol A dimethacrylate (BisEMA) (Formula I), preferably, said Ethoxylated bisphenol A dimethacrylate comprises ethoxyl chain with n=2, and m=2, 4 or 10;

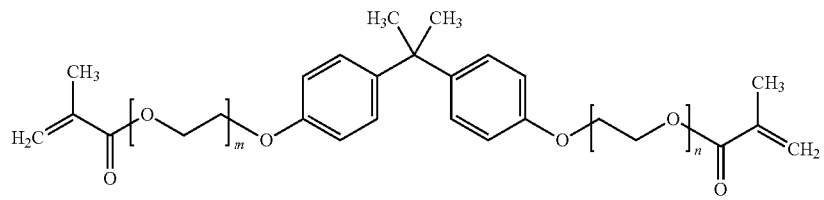

Formula I about 0 to 75 wt % Diurethane dimethacrylate (UDMA) (Formula II);

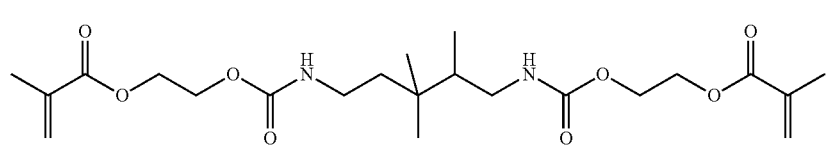

Formula II about 0 to about 10 wt % Triethylene glycol dimethacrylate (TEGDMA) (Formula III); and

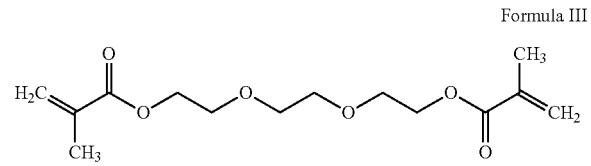 [SMILES: C=C(C)C(=O)OCCOCCOCCOC(=O)C(=C)C]

Formula III about 0.01 to about 10 wt % of a photo-initiator, preferably, the photo-initiator is Diphenyl (2,4,6-trimethylbenzoyl) phosphine oxide (TPO).

Preferably, said compound further composing: about 0 to about 10 wt % of Trimethylolpropane triacrylate (TMPTA) (Formula IV);

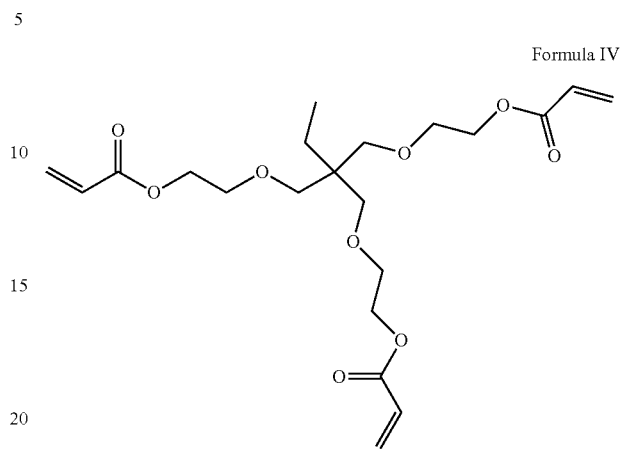

Formula IV

In one embodiment, the three-dimensional printing article for making dental products, comprising: a photoresist, wherein the photoresist is consisted of about 0.1 to about 10 wt % of silicon dioxide or silylated silicon dioxide, and about 0.01 to about 1 wt % of titanium dioxide.

In one embodiment, the three-dimensional printing article for making dental products, comprising: a toner, wherein the toner is selected from the group consisting of ferroso ferric oxide, iron(III) oxide-hydroxide, anhydrous iron oxide, anhydrous iron (III) oxide, hydrated iron oxide, ferrous oxide, ferric oxide, and iron (II, III) oxide.

Preferably, the toner is consisted of about 0.01 to about 0.05 wt % of ferrihydrite (III), or about 0.001 to about 0.005 wt % of iron trioxide.

Figure 1:
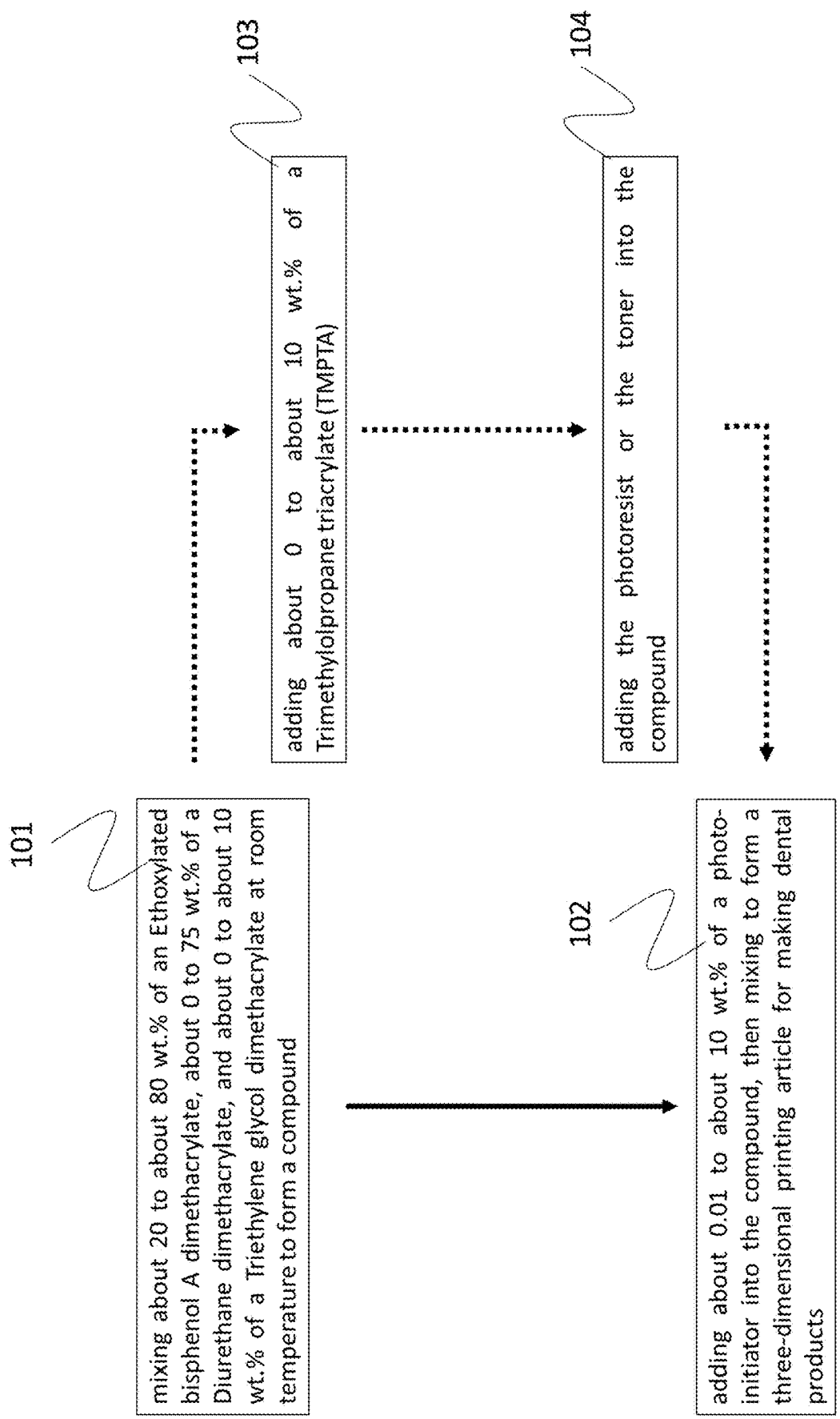
FIG. 1 is a flow chart of the method to prepare the present invention of a three-dimensional printing article for making dental products.

The present invention further provides a method for preparing the three-dimensional printing article for making dental products. Please refer to FIG. 1, the method comprising: (a) mixing about 20 to about 80 wt % of an Ethoxylated bisphenol A dimethacrylate, about 0 to 75 wt % of a Diurethane dimethacrylate, and about 0 to about 10 wt % of a Triethylene glycol dimethacrylate at room temperature to form a compound, step 101; and (b) adding about 0.01 to about 10 wt % of a photo-initiator into the compound, then mixing to form a three-dimensional printing article for making dental products, step 102.

Preferably, the step (a) further composing: (a1) adding about 0 to about 10 wt % of a Trimethylolpropane triacrylate (TMPTA), step 103.

Preferably, the step (a) further composing: (a2) adding a photoresist or a toner into the compound, wherein the photoresist chosen from about 0.1 to about 10 wt % of silicon dioxide or silylated silicon dioxide, or about 0.01 to about 1 wt % of titanium dioxide, wherein the toner chosen from about 0.01 to about 0.05 wt % of ferrihydrite (III), or about 0.001 to about 0.005 wt % of iron trioxide, step 104.

Figure 3:
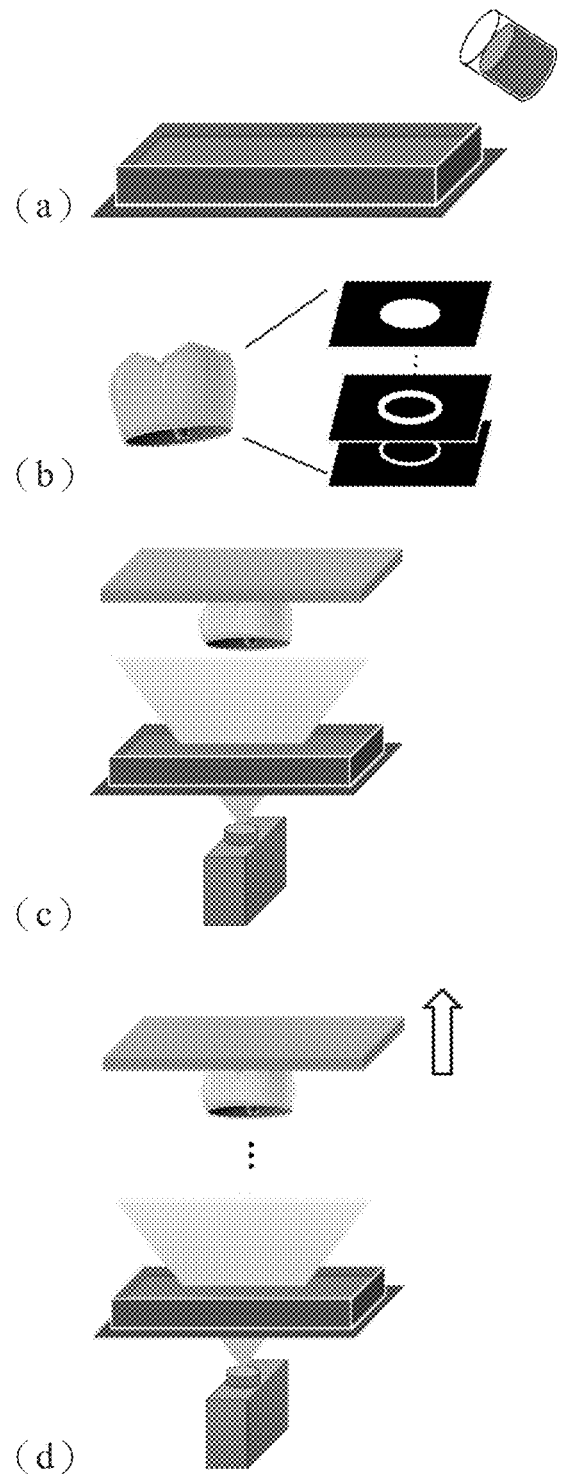
FIG. 3 is an illustration of the method to make dental products using the three-dimensional printing article of the present invention.

The present invention further provides a method to make dental products using said three-dimensional printing article. Please refer to FIG. 2 and FIG. 3, the method comprising: (a) pouring the three-dimensional printing article for making dental products into a container, step 201; (b) obtaining a plurality of continuously sectional drawings of a dental prosthesis simple, wherein there is a sectional distance of the dental prosthesis simple between each drawing, step 202; (c) choosing the top of the drawings, forming a sheet model as the chosen drawing through focusing an intensive irradiation light source on the bottom of the container, step 203; and (d) moving the sheet model upward for the sectional distance, and repeating step (c) through choosing the next of the drawings until the bottom of the drawings, each of the sheet models is sequentially stacked to form the dental prosthesis, step 204.

Preferably, in the step 203, the intensive irradiation light source is with wavelength ranging from 256 to 500 nm focusing on the bottom of the container for 1~8 seconds.

In one embodiment, the present invention further tests the characteristics of the three-dimensional printing article for making dental products to disclose (1) surface microhardness: when the load of the indenor is 0.1 kg and the sample sheet is pressed for 25 seconds, the measured result of the surface microhardness of the present invention of dental material (Vickers hardness test, HMV-2, Shimadzu, Kyoto, Japan) is 15.9 HV; and (2) bending resistance: a three-point bending test is conducted through a universal material testing machine (AGS-500G, Shimadzu, Kyoto, Japan) to test the stress tolerance. The testing machine is mounted with a load cell of 100 kg, distance between the two supporting frames is 25 mm, falling speed of the load cell is 2 mm per minute, the measured bending resistance is 97.4 MPa, the measured flexural modulus is 1827 MPa.

Although the present invention has been described in terms of specific exemplary embodiments and examples, it will be appreciated that the embodiments disclosed herein are for illustrative purposes only and various modifications and alterations might be made by those skilled in the art without departing from the spirit and scope of the invention as set forth in the following claims.

What is claimed is:

1. A three-dimensional printing article for making dental products, comprising a composition, wherein the composition comprises:
   an Ethoxylated bisphenol A dimethacrylate, a Diurethane dimethacrylate and a Triethylene glycol dimethacrylate with 20 to 80 wt %:0 to 75 wt %:0 to 10 wt % of the composition;
   a toner, wherein the toner consists of ferrihydrite (III) with 0.01 to 0.05 wt % of the composition, or iron trioxide with 0.001 to 0.005 wt % of the composition; and
   a photo-initiator, wherein the photo-initiator is with 0.01 to 10 wt % of the composition.

2. The article of claim 1, wherein the composition further comprising: a Trimethylolpropane triacrylate (TMPTA) with 0 to 10 wt % of the compound.

3. The article of claim 1, wherein the Ethoxylated bisphenol A Dimethacrylate has a chemical formula as the following:

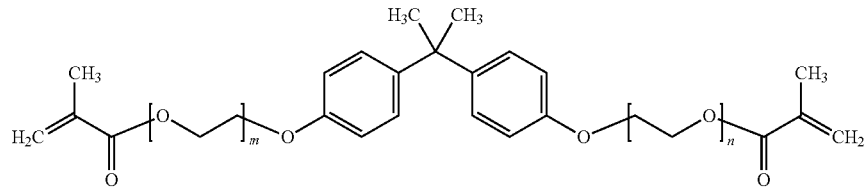

and has two ethoxyl chains with n, m=2, 4 or 10.

4. The article of claim 1, wherein the photo-initiator is Diphenyl (2, 4, 6-trimethylbenzoyl) phosphine oxide (TPO).

5. The article of claim 1, wherein the composition further comprises a photoresist, wherein the photoresist consists of silicon dioxide or silylated silicon dioxide with 0.1 to 10 wt % of the composition, and titanium dioxide with 0.01 to 1 wt % of the composition.

6. A method for preparing an article of claim 1, wherein the method composing:
   (a) mixing an Ethoxylated bisphenol A dimethacrylate, a Diurethane dimethacrylate, and a Triethylene glycol dimethacrylate to form a compound at room temperature with 20 to 80 wt %:0 to 75 wt %:0 to 10 wt % of the composition,
   (b) adding a toner and a photo-initiator to the composition, then mixing to form an article of claim 1, wherein the photo-initiator is with 0.01 to 10 wt % of the compound.

7. The method of claim 6, wherein the step (a) further comprising:
   (a1) adding a Trimethylolpropane triacrylate (TMPTA), with 0 to 10 wt %:of the compound.

8. The method of claim 6, wherein the step (a) further comprising:
   (a2) adding a photoresist or a toner into the compound, wherein the photoresist wherein the photoresist is consisted of silicon dioxide or silylated silicon dioxide with 0.1 to 10 wt % of the compound, and titanium dioxide with 0.01 to 1 wt % of the compound, wherein the toner is consisted of ferrihydrite (III) with 0.01 to 0.05 wt % of the compound, or iron trioxide with 0.001 to 0.005 wt % of the compound.

9. A method for preparing a dental prosthesis, wherein the method comprising:

(a) pouring an article of claim 1 into a container;
(b) obtaining a plurality of continuously sectional drawings of a dental prosthesis simple, wherein there is a sectional distance of the dental prosthesis simple between each drawing;
(c) choosing the top of the drawings, forming a sheet model as the chosen drawing through focusing an intensive irradiation light source on the bottom of the container; and
(d) moving the sheet model upward for the sectional distance, and repeating step (c) through choosing the next of the drawings until the bottom of the drawings, each of the sheet models is sequentially stacked to form the dental prosthesis.

10. The method of claim 9, wherein in the step (c), the intensive irradiation light source is with wavelength ranging from 256 to 500 nm focusing on the bottom of the container for 1~8 seconds.

\* \* \* \* \*